US010028752B2

(12) United States Patent
Carver et al.

(10) Patent No.: US 10,028,752 B2
(45) Date of Patent: Jul. 24, 2018

(54) BROSTEOTOME AND METHOD OF USE

(71) Applicant: DePuy Synthes Products, Inc., Raynham, MA (US)

(72) Inventors: Adam Carver, Warsaw, IN (US); Jeremiah Lewis, Leesburg, IN (US); Conrad Klotz, Nappanee, IN (US); Jenna Ross, Warsaw, IN (US); Chad Lawrence, Warsaw, IN (US)

(73) Assignee: DePuy Synthes Products, Inc., Raynham, MA (US)

(*) Notice: Subject to any disclaimer, the term of this patent is extended or adjusted under 35 U.S.C. 154(b) by 846 days.

(21) Appl. No.: 14/506,582

(22) Filed: Oct. 3, 2014

(65) Prior Publication Data

US 2016/0095606 A1 Apr. 7, 2016

(51) Int. Cl.
*A61B 17/88* (2006.01)
*A61B 17/16* (2006.01)

(52) U.S. Cl.
CPC ........ *A61B 17/164* (2013.01); *A61B 17/1659* (2013.01)

(58) Field of Classification Search
CPC ............ A61B 17/1659; A61B 17/1664; A61B 17/1668
USPC ...................................................... 606/83–85
See application file for complete search history.

(56) References Cited

U.S. PATENT DOCUMENTS

D211,323 S 6/1968 Falk
4,306,550 A * 12/1981 Forte .................. A61B 17/1659 30/276
5,041,118 A * 8/1991 Wasilewski ........ A61B 17/1668 606/85
D372,311 S 7/1996 Koros et al.
5,665,091 A * 9/1997 Noble ................ A61B 17/1659 606/79
5,814,049 A * 9/1998 Pratt .................. A61B 17/1666 606/79
D443,360 S 6/2001 Haberland
D449,887 S 10/2001 Haberland et al.
6,319,256 B1 * 11/2001 Spotorno ........... A61B 17/1659 606/79
D469,871 S 2/2003 Sand
D594,119 S 6/2009 Berberich et al.
D594,121 S 6/2009 Berberich et al.
D700,322 S 2/2014 Kleiner
D714,934 S 10/2014 Kawamura
8,870,875 B2 * 10/2014 Romagnoli ........ A61B 17/1659 606/85
8,932,249 B2 1/2015 Parihar et al.
D726,907 S 4/2015 Trump
2004/0116933 A1 * 6/2004 White ................ A61B 17/1668 606/85

(Continued)

*Primary Examiner* — Matthew Lawson

(74) *Attorney, Agent, or Firm* — Barnes & Thornburg LLP

(57) ABSTRACT

An orthopedic surgical instrument that includes an elongated body having a longitudinal axis extending through a distal end and a proximal end, and a plurality of cutting teeth are extending from a medial side of the elongated body. Each cutting tooth includes a first curved medial edge, and a curved outer surface that extends distally from the first curved medial edge to a second curved medial edge. When the instrument is viewed in a coronal plane, the curved outer surface of each medial cutting tooth extends parallel to the longitudinal axis of the elongated body.

17 Claims, 9 Drawing Sheets

(56) References Cited

U.S. PATENT DOCUMENTS

| | | | |
|---|---|---|---|
| 2008/0200915 | A1 | 8/2008 | Globerman et al. |
| 2012/0136381 | A1 | 5/2012 | Morrison et al. |

* cited by examiner

BROSTEOTOME AND METHOD OF USE

Cross-reference is made to co-pending U.S. Design patent application Ser. No. 29/504,342 entitled "BROSTEOTOME" by Adam Carver et al., filed Oct. 3, 2014, and issued as U.S. Design Pat. No. D740,938, which is assigned to the same assignee as the present application and which is hereby incorporated by reference.

TECHNICAL FIELD

The present disclosure relates generally to orthopaedic surgical instruments and, more particularly, to surgical instruments used with a patient's humerus.

BACKGROUND

During the lifetime of a patient, it may be necessary to perform a shoulder replacement procedure on the patient as a result of, for example, disease or trauma. In a shoulder replacement procedure, a humeral prosthesis is used to replace the natural head of the patient's humerus. The humeral prosthesis typically includes an elongated stem component that is implanted into the intramedullary canal of the patient's humerus and a generally hemispherically-shaped prosthetic head component that is secured to the stem component. In some shoulder replacement procedures, the natural glenoid surface of the scapula may be resurfaced or otherwise replaced with a glenoid component that provides a bearing surface upon which the prosthetic head component of the humeral prosthesis articulates.

SUMMARY

According to one aspect of the disclosure, an orthopaedic surgical instrument for preparing a patient's humeral bone to receive an orthopaedic implant is disclosed. The instrument comprises an elongated body having a longitudinal axis extending through a distal end and a proximal end, a first plurality of cutting teeth extending outwardly from an anterior surface of the elongated body, a second plurality of cutting teeth extending outwardly from a posterior surface of the elongated body, and a plurality of medial cutting teeth extending from a medial side of the elongated body. Each medial cutting tooth comprises a first curved medial edge and a curved outer surface that extends distally from the first curved medial edge to a second curved medial edge. The curved outer surface of each medial cutting tooth extends parallel to the longitudinal axis of the elongated body when the instrument is viewed in a coronal plane.

In some embodiments, an imaginary line may extend through a medial-most point of the first curved medial edge and a medial-most point of the second curved medial edge of each medial cutting tooth, and the imaginary line of each medial cutting tooth may extend parallel to the longitudinal axis of the elongated body and is spaced apart from the imaginary lines defined by the other medial cutting teeth.

In some embodiments, the plurality of medial cutting teeth may include a distal-most medial cutting tooth, and the imaginary line of the distal-most medial cutting tooth may be positioned laterally of the imaginary line of any other medial cutting tooth of the plurality of medial cutting teeth.

Additionally, in some embodiments, the orthopaedic surgical instrument may further comprise a slot defined between each pair of adjacent medial cutting teeth of the plurality of medial cutting teeth. Each slot may include a distal-facing opening. In some embodiments, each slot may be defined between a planar distal surface and a planar proximal surface that extends parallel to the planar distal surface. In some embodiments, the planar distal surface and the planar proximal surface of each slot may extend parallel to the planar distal surfaces and the planar proximal surfaces of the other slots.

In some embodiments, an angle may be defined between each distal surface and the longitudinal axis of the elongated body when the instrument is viewed in the coronal plane. The angle may have a magnitude of 45 degrees.

In some embodiments, a curved base surface may connect the planar distal surface to the planar proximal surface. In some embodiments, each slot may have a height defined by an imaginary line extending orthogonal to the planar distal surface and the planar proximal surface. Each medial cutting tooth may have a thickness defined between a medial-most point of its first curved medial edge and a medial-most point of its second curved medial edge. The thickness of each medial cutting tooth may be less than the height of each slot. Additionally, in some embodiments, the thicknesses of the medial cutting teeth are equal.

In some embodiments, the curved outer surface of each medial cutting tooth may extend from the anterior surface to the posterior surface of the elongated body.

In some embodiments, the orthopaedic surgical instrument may further comprise a handle extending from the proximal end of the elongated body and a proximal strike plate attached to the handle. Additionally, in some embodiments, the orthopaedic surgical instrument may further comprise a distal stem removeably coupled to the distal end of the elongated body.

In some embodiments, an alignment hole may be defined in the elongated body. The alignment hole may extend from a first opening in the anterior surface to a second opening in the posterior surface. The alignment hole may be sized to receive an alignment pin.

According to another aspect, an orthopaedic surgical instrument for preparing a patient's humeral bone to receive an orthopaedic implant comprises an elongated body having a longitudinal axis extending through a distal end and a proximal end, and a plurality of cutting teeth extending from a medial side of the elongated body. Each cutting tooth comprises a first curved medial edge and a curved outer surface that extends distally from the first curved medial edge to a second curved medial edge. When the instrument is viewed in a coronal plane, the curved outer surface of each medial cutting tooth extends parallel to the longitudinal axis of the elongated body, and an arced imaginary line is defined by the medial-most points of the second curved medial edges of the cutting teeth. The elongated body has a lateral surface positioned opposite the medial surface that is devoid of cutting teeth.

In some embodiments, the orthopaedic surgical instrument may further comprise a handle extending from the proximal end of the elongated body and a proximal strike plate attached to the handle. The orthopaedic surgical instrument may further comprise a distal stem coupled to the distal end of the elongated body.

In some embodiments, the orthopaedic surgical instrument may further include a first plurality of tapered cutting teeth extending outwardly from an anterior surface of the elongated body and a second plurality of tapered cutting teeth extending outwardly from a posterior surface of the elongated body.

According to another aspect, a method of preparing a patient's humeral bone to receive an orthopaedic implant is disclosed. The method comprises inserting an orthopaedic surgical instrument into the patient's humeral bone to define a cavity sized to receive the orthopaedic implant. The orthopaedic surgical instrument includes a plurality of medial cutting teeth positioned to define a curved medial surface in the patient's humeral bone, a plurality of anterior cutting teeth to define a first tapered groove of the cavity, and a plurality of posterior cutting teeth to define a second tapered groove on a posterior side. The method also comprises inserting the orthopaedic implant into the cavity such that a first keel of the orthopaedic implant is received in the first tapered groove and a second keel of the orthopaedic implant is received in the second tapered groove. The orthopaedic implant further includes a curved medial surface that substantially matches the curved medial surface defined by the plurality of medial cutting teeth of the orthopaedic surgical instrument.

In some embodiments, inserting the orthopaedic surgical instrument may include inserting an elongated stem into the patient's humeral bone. In some embodiments, the method may also include removing a bone wafer from a slot defined between a pair of medial cutting teeth.

BRIEF DESCRIPTION OF THE DRAWINGS

The detailed description particularly refers to the following figures, in which.

DETAILED DESCRIPTION OF THE DRAWINGS

Figure 1:
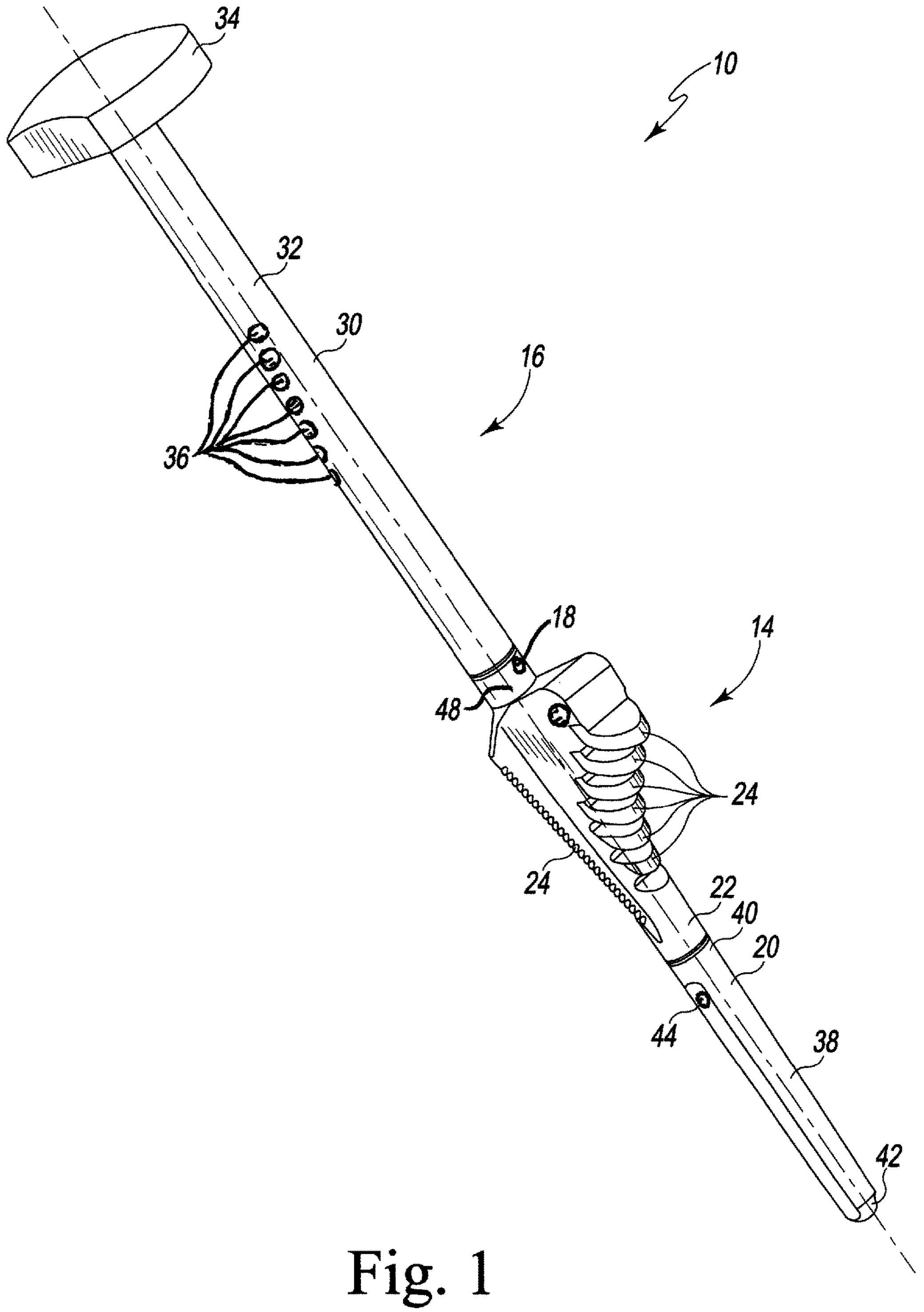
FIG. 1 is a perspective view of an orthopaedic surgical instrument for use in preparing a patient's humeral bone to receive a humeral prosthetic component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopedics. Use of such anatomical reference terms in the written description and claims is intended to be consistent with their well-understood meanings unless noted otherwise.

Referring now to FIG. 1, an orthopaedic surgical instrument 10 for use in preparing a patient's bone to receive an orthopaedic implant is shown. In the illustrative embodiment, the instrument 10 is a brosteotome configured for use in preparing a patient's humeral bone to receive the humeral prosthetic component 12 shown in FIGS. 5-6. The brosteotome 10 includes an elongated body 14, a handle 16 extending from a proximal end 18 of the elongated body 14, and an intramedullary rod or stem 20 extending from a distal end 22 of the body 14. As described in greater detail below, the brosteotome 10 also includes cutting teeth 24 that are shaped and arranged to form a cavity in the patient's humeral bone sized to receive the humeral prosthetic component 12.

The components of the brosteotome 10 (i.e., the body 14, the handle 16, and the stem 20) are illustratively formed separately from a metallic material such as, for example, stainless steel. The components are then assembled together to form the brosteotome 10. In other embodiments, one or more of the brosteotome components may be partially or wholly formed from a polymeric material such as plastic. For example, the body 14 may be formed from plastic that is injected molded onto cutting teeth formed from metal. It should be appreciated that in other embodiments, the brosteotome may be formed as a single monolithic component.

The handle 16 of the brosteotome 10 includes an elongated shaft 30 that extends from the end 18 of the brosteotome body 14. The shaft 30 has a cylindrical outer surface 32 that is configured to be gripped by a surgeon or other user. A plate 34 is secured at the proximal end of the elongated shaft 30. In the illustrative embodiment, the plate 34 is sized to be struck by a mallet (not shown) or other tool during a surgical procedure to drive the brosteotome 10 into the patient's bone. In that way, the plate 34 acts a "strike plate" for the brosteotome 10. The plate 34 is oversized relative to the elongated shaft 30 to protect a user's hand when gripping the shaft 30. As shown in FIG. 1, a plurality of alignment holes 36 are defined in the elongated shaft 30. Each alignment hole 36 is sized to receive an orientation guide pin (not shown). The position of each alignment hole 36 on the outer surface 32 corresponds to a possible version of the humeral prosthetic component 12, which a surgeon may select to optimize deltoid function for a particular patient.

As described above, the intramedullary rod or stem 20 of the brosteotome 10 extends from the distal end 22 of the elongated body 14. The stem 20 includes an elongated shaft 38 that has a proximal end 40 attached to the elongated body 14. In the illustrative embodiment, the proximal end 40 of the shaft 38 is threaded into the distal end 22 of the elongated body 14 to removeably couple the stem 20 to the elongated body 14. In other embodiments, the stem 20 may be permanently fixed to the elongated body 14. As shown in FIG. 1, the elongated shaft 38 of the stem 20 extends away from the proximal end 40 to a distal tip 42, and the shaft 38 has a cross-sectional diameter that corresponds to the cross-sectional diameter of the humeral prosthetic component 12 to be implanted into the patient's humerus.

The stem 20 also has an alignment pin hole 44 defined in the elongated shaft 38 near the proximal end 40. The alignment hole 44 is sized to receive an orientation guide pin (not shown). The position of the alignment hole 44 on the shaft 38, like the alignment holes 36 described above, corresponds to a desired version of the humeral prosthetic component 12. It should be appreciated that in other embodiments the stem 20 may include additional alignment holes 44 corresponding to other possible versions for the humeral prosthetic component 12.

Figure 2:
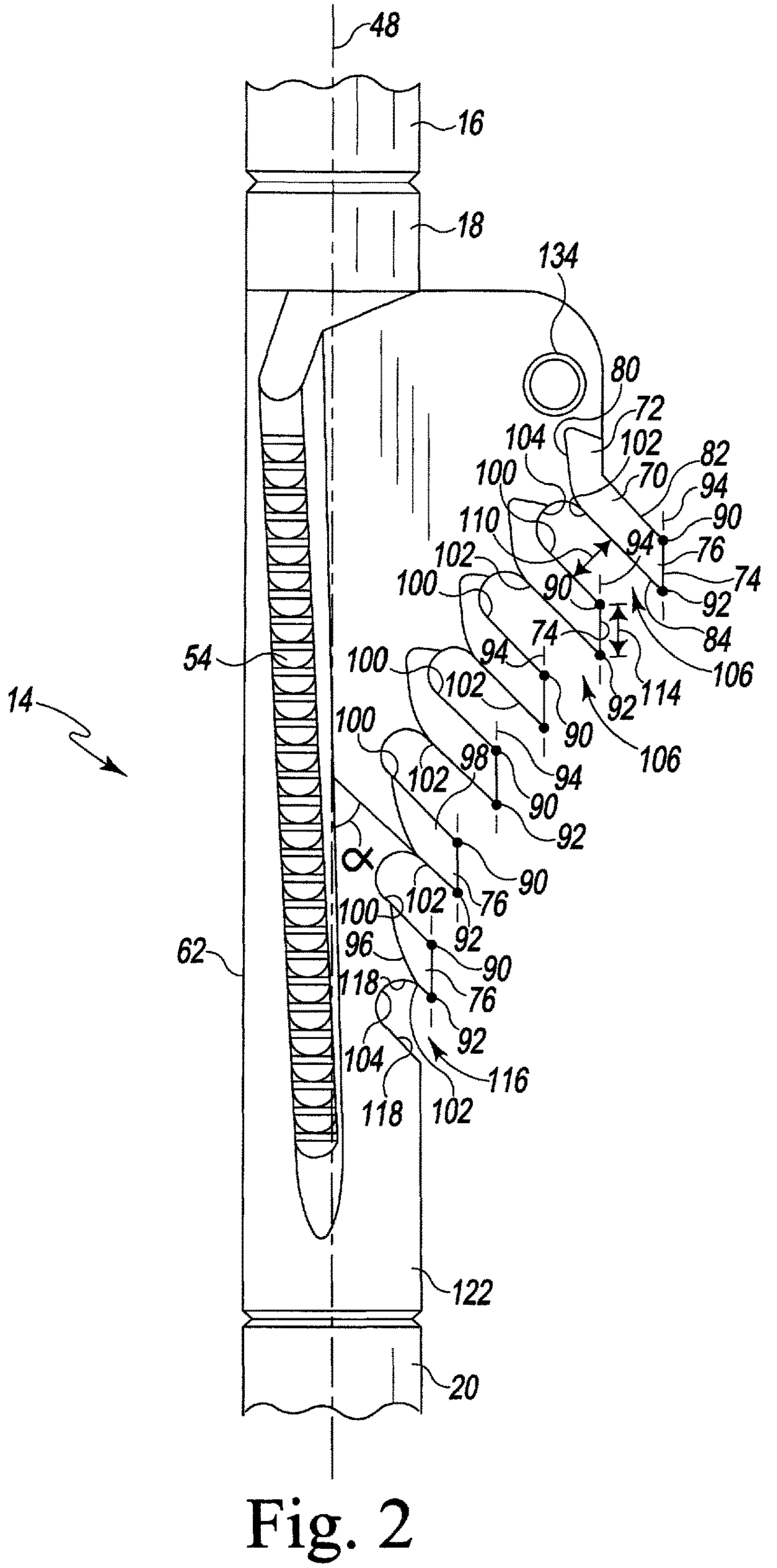
FIG. 2 is an elevation view of the orthopaedic surgical instrument of FIG. 1 positioned in a coronal plane.
Figure 3:
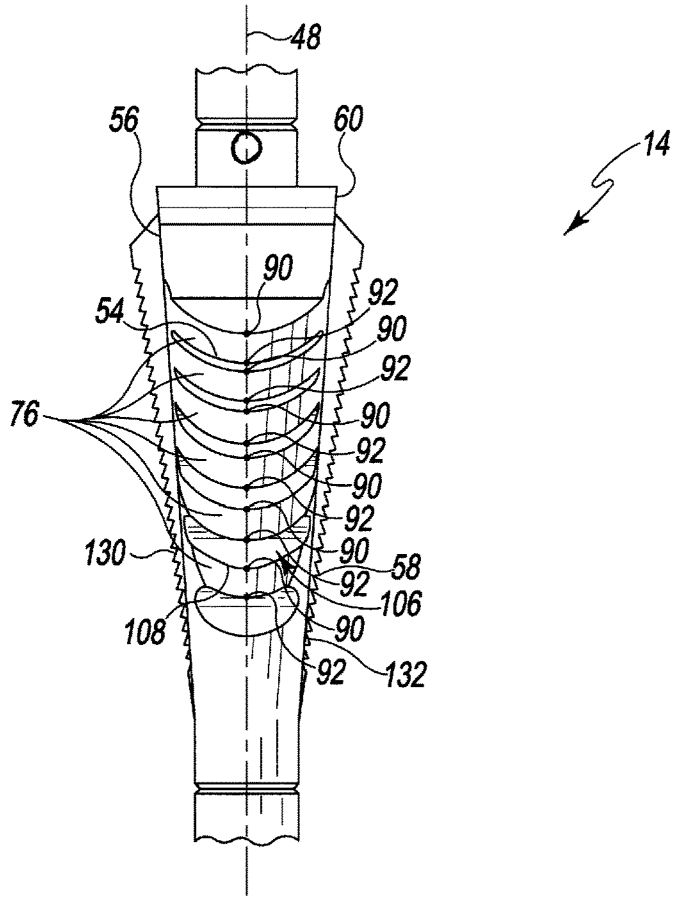
FIG. 3 is another elevation view showing the medial side of the orthopaedic surgical instrument of FIG. 1.

As shown in FIGS. 2-3, the distal end 22 of the elongated body 14 of the brosteotome 10 is cylindrical and has a cross-sectional diameter equal to the shaft 38 of the stem 20. The opposite proximal end 18 of the elongated body 14 is also cylindrical and has a cross-sectional diameter equal to the shaft 30 of the handle 16. The elongated body 14 has a longitudinal axis 48 that extends through the proximal end 18 and the distal end 22. As described in greater detail below, the longitudinal axis 48 defines the axis of insertion of the brosteotome 10 during a surgical procedure.

Figure 4:
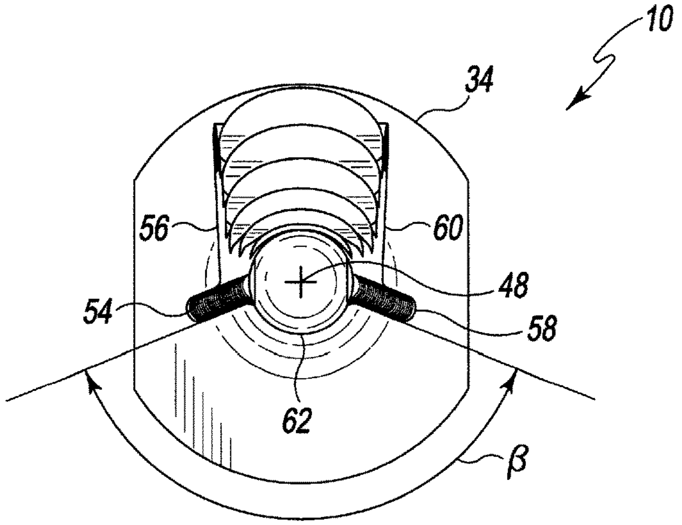
FIG. 4 is a plan view of the orthopaedic surgical instrument of FIG. 1.

As described above, the brosteotome 10 includes a plurality of cutting teeth 24 configured to resect the proximal end of a patient's humerus. The cutting teeth 24 include a set of medial cutting teeth 50 extending from a medial side 52 of the elongated body 14, a set of anterior cutting teeth 54 extending from an anterior surface 56 of the elongated body 14, and a set of posterior cutting teeth 58 extending from a posterior surface 60 of the elongated body 14. As shown in FIGS. 2 and 4, the elongated body 14 further includes a lateral surface 62 extending between the anterior cutting teeth 54 and posterior cutting teeth 58. In the illustrative embodiment, the lateral surface 62 is curved and is devoid of cutting teeth.

Each medial cutting tooth 50 includes a flange 70 that extends from a base 72 attached to the medial side 52 of the elongated body 14 to a medial tooth tip 74. Each tooth 50 also has a curved outer surface 76 that extends from a posterior edge 78 connected to the elongated body 14 to an anterior edge 80 connected to the elongated body 14. As shown in FIGS. 2-3, the curved outer surface 76 also extends between a pair of curved medial edges—a proximal edge 82 and a distal edge 84. As shown in FIGS. 2-3, the curved outer surface 76 extends parallel to the longitudinal axis 48 of the elongated body 14 to facilitate cutting the bone, as described in greater detail below.

As shown in FIGS. 2-3, each tooth 50 has a medial-most point 90 on the proximal edge 82 of the curved outer surface 76 and another medial-most point 92 on the distal edge 84 of the curved outer surface 76. An imaginary line 94 extends through the points 90, 92 parallel to the longitudinal axis 48 of the elongated body 14. As shown in FIG. 2, the imaginary lines 94 of the teeth 50 are spaced apart in a medial-lateral direction. For example, the imaginary line 94 defined by the distal-most tooth 50 (i.e., tooth 96) is spaced apart laterally from the imaginary line 94 of its adjacent tooth 98. As shown in FIG. 3, the imaginary lines 94 of the teeth 50 are coincident when viewed in a sagittal plane.

The tooth flange 70 of each tooth 50 includes a proximal surface 100 that extends outwardly from its tooth base 72 to the proximal edge 82 of that tooth. The tooth flange 70 of each tooth 50 also includes a distal surface 102 positioned opposite the proximal surface 100. The distal surface 102 of each tooth 50 extends outwardly from the tooth base 72 to the distal edge 84 of that tooth. In the illustrative embodiment, the proximal surface 100 and the distal surface 102 of each tooth 50 are planar surfaces that extend parallel to one another. In other embodiments, one or both of the surfaces 100, 102 may be curved or arced.

As shown in FIG. 2, a curved surface 104 extends between the proximal surface 100 each tooth 50 and the distal surface 102 of its adjacent tooth 50. Each of the surfaces 100, 102, and 104 cooperate to define a slot 106 between each pair of adjacent cutting teeth 50. In the illustrative embodiment, each slot 106 has a distal-facing opening 108 that received bone resected by the cutting teeth 50, and the distal-facing opening 108 has a height 110 that is defined between an adjacent proximal surface 100 and distal surface 102. As shown in FIG. 2, the height 110 of each opening 108 (and hence each slot 106) is illustrated by an imaginary line extending orthogonal to the surfaces 100, 102. In the illustrative embodiment, the heights 110 are equal.

Each cutting tooth 50 has a thickness 114 defined between the medial-medial-most point 90 on its proximal edge 82 and the medial-most point 92 on its distal edge 84. In the illustrative embodiment, the cutting teeth 50 have the same thickness 114. Additionally, in the illustrative embodiment, the distal-facing openings 108 of the slots 106 are sized to be larger than the cutting teeth 50. In other words, the height 110 of each slot 106 is greater than the thickness 114 of each cutting tooth 50. In other embodiments, the heights of at least some of the slots may be smaller than the thicknesses of some of the teeth. As described in greater detail below, the size of each slot 106 compacts bone resected from the humerus into wafers 200 suitable for use in bone graft impaction.

As shown in FIGS. 2-3, an additional slot 116 is defined below the distal-most tooth 96. The slot 116 extends parallel to the other slots 106 and has a substantially similar configuration. For example, the slot 116 is defined between a pair of planar surfaces 118 that are connected by a curved surface 104.

Figure 7:
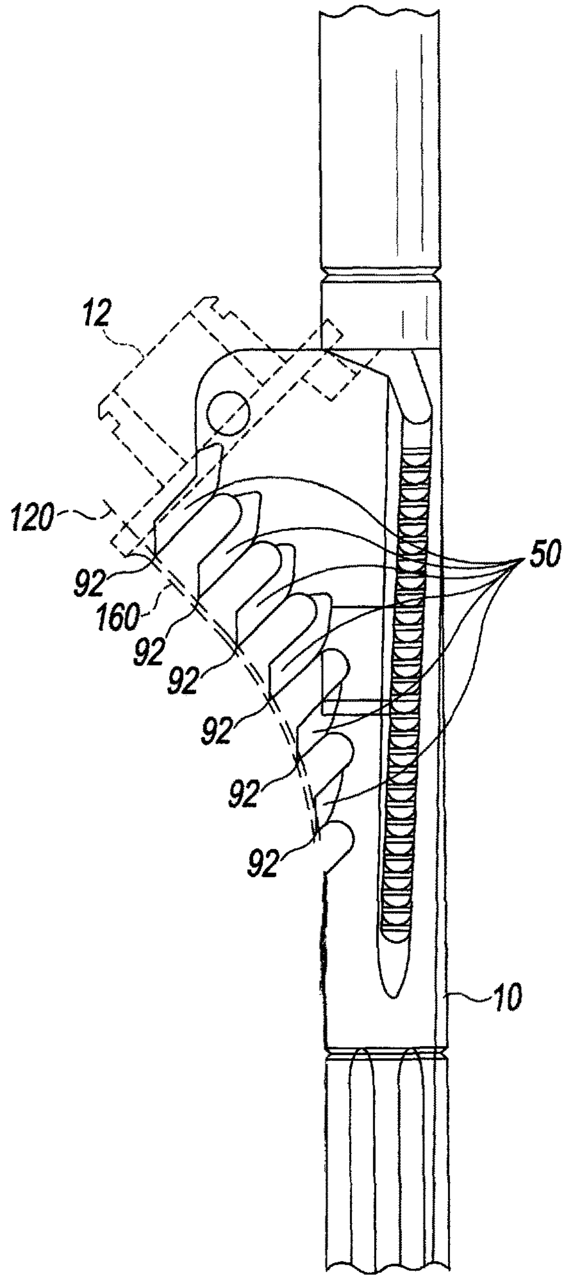
FIG. 7 is a partial elevation view of the orthopaedic surgical instrument of FIG. 1 and an outline of the humeral prosthetic component superimposed on the orthopaedic surgical instrument.

As shown in FIG. 2, the cutting teeth 50 extend at an angle $\alpha$ relative to the longitudinal axis 48 when the brosteotome 10 is viewed in the coronal plane. In the illustrative embodiment, the angle $\alpha$ has a magnitude of about 45 degrees. Additionally, the medial-most points 92 on the distal-edges 84 define an arced imaginary line 120 that extends medially away from the elongated body 14, as shown in FIG. 7. As described in greater detail below, the arced imaginary line 120 substantially matches a corresponding curved medial surface 122 of the humeral prosthetic component 12.

As described above, the brosteotome 10 also includes a set of anterior cutting teeth 54 and a set of posterior cutting teeth 58. As shown in FIGS. 3-4, the anterior cutting teeth 54 extend from the anterior surface 56 of the elongated body 14. The anterior cutting teeth 54 cooperate to define a tapered cutting edge 130. Similarly, the posterior cutting teeth 58 extend from the posterior surface 60 of the elongated body 14 and define a tapered cutting edge 132. As shown in FIG. 4, an angle $\beta$ is defined between the cutting teeth 54, 58. In the illustrative embodiment, the angle $\beta$ matches the angle $\tau$ defined between the fins 150, 152 of the humeral prosthetic component 14.

In the illustrative embodiment, the brosteotome 10 also includes a depth stop hole 134 that extends through the anterior surface 56 and the posterior surface 60 of the elongated body 14. The depth stop hole 134 is sized to receive a cylindrical pin 136 (see FIG. 9) that acts as depth stop for the brosteotome 10 during a surgical procedure. As described in greater detail below, the brosteotome 10 is impacted until the pin 136 contacts a resected proximal surface of a patient's humeral bone.

Figure 5:
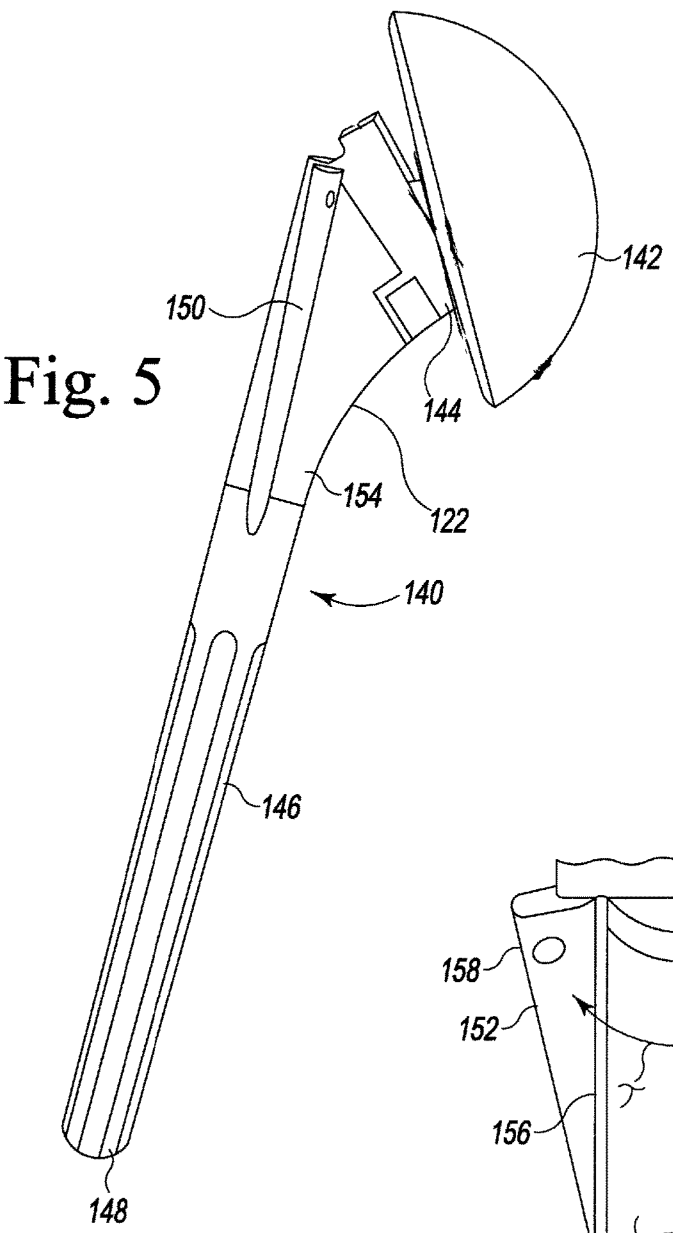
FIG. 5 is a side elevation view of a humeral prosthetic component.
Figure 6:
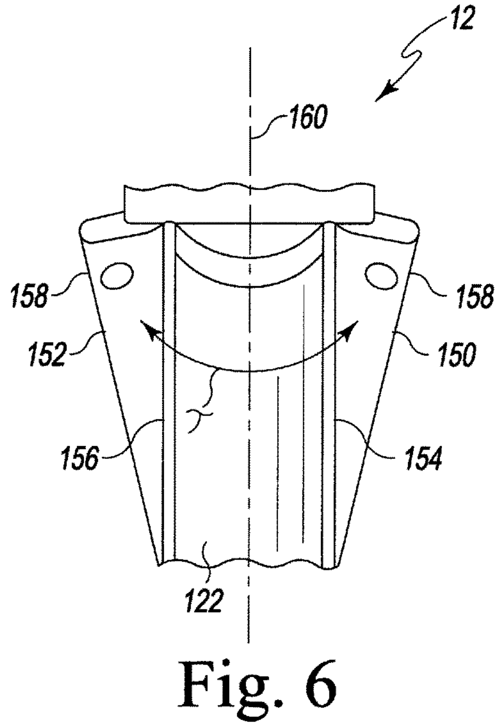
FIG. 6 is a partial elevation view showing the medial side of the humeral prosthetic component of FIG. 5.

As described above, the brosteotome 10 is configured for use in preparing a patient's humeral bone to receive the humeral prosthetic component 12 shown in FIGS. 5-6. In the illustrative embodiment, the prosthetic component 12 includes an elongated stem 140 configured to be implanted into the proximal end of a patient's humerus and a humeral head component 142 that is secured to the proximal end 144 of the elongated stem 140. In the illustrative embodiment, the stem 140 and humeral head component 142 are separately formed as single, monolithic components from an implant-grade metallic material such as, for example, cobalt chromium.

As shown in FIG. 5, the elongated stem 140 includes a body 146 that extends from the proximal end 144 to a distal tip 148. A pair of fins 150, 152 extend outwardly from the anterior surface 154 and the posterior surface 156, respectively, of the body 146. Each of the fins 150, 152 include a tapered outer edge 158. As described above, an angle τ is defined between the fins 150, 152.

As shown in FIG. 5, the body 146 includes a medial surface 122 that defines an arc 160 when the stem 140 is viewed in a coronal plane. As described above and shown in FIG. 7, the arc 160 substantially matches the arced imaginary line 120 defined by the medial cutting teeth 50 of the brosteotome 10. In that way, the brosteotome 10 is configured to resect the patient's humeral bone and shape the bone to receive the stem 140, as described in greater detail below.

Figure 8:
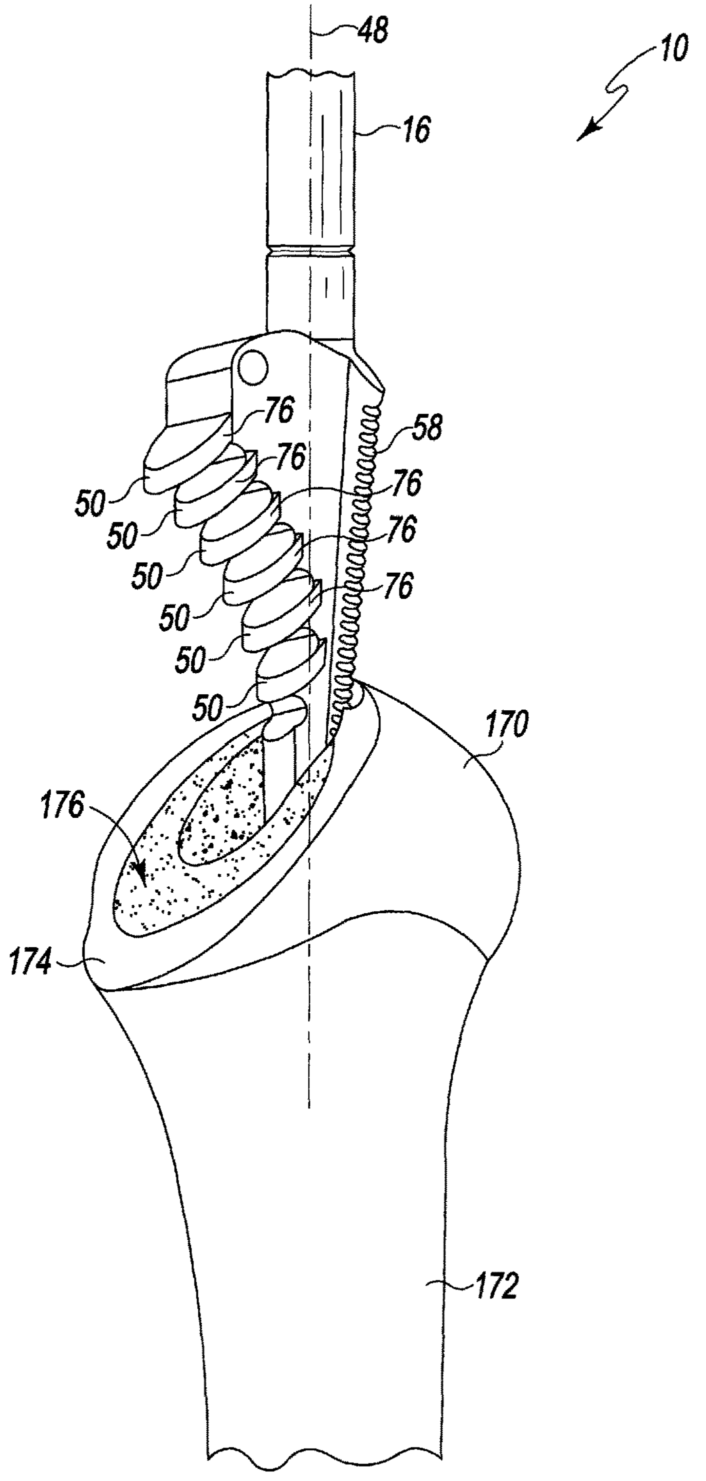
FIGS. 8-10 are illustrations of a surgical procedure for using the orthopaedic surgical instrument of FIG. 1 in preparing a patient's humeral bone to receive the humeral prosthetic component of FIG. 5.
Figure 9:
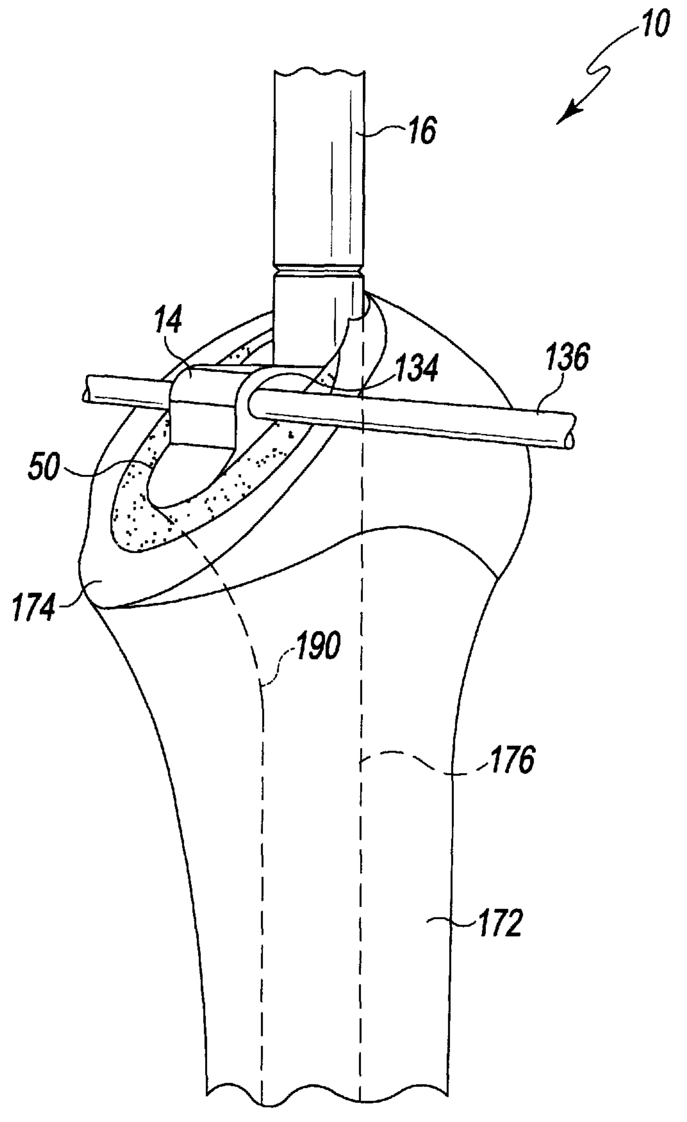
Figure 10:
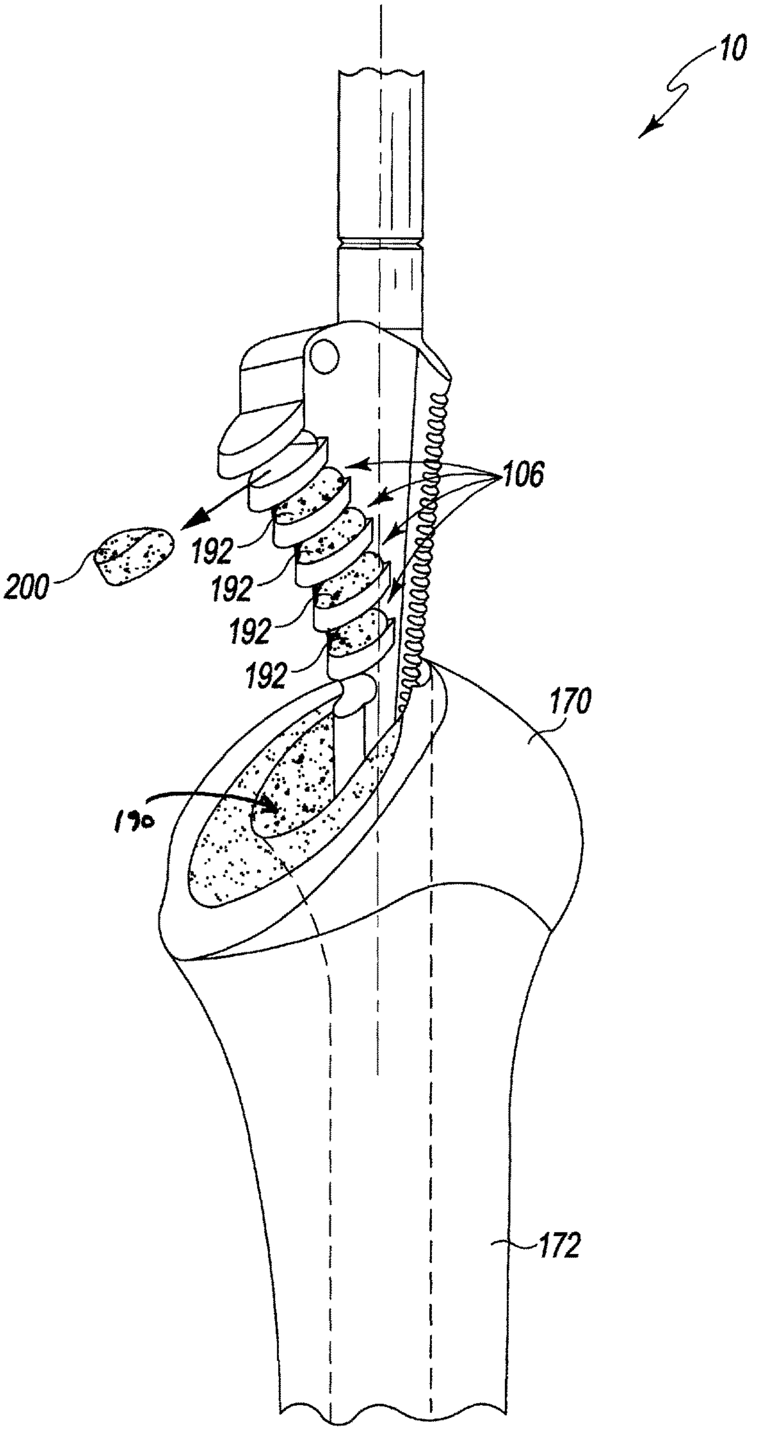

Referring now to FIGS. 8-10, the brosteotome 10 is shown in use in preparing a proximal end 170 of a patient's humeral bone 172 to receive the humeral prosthetic component 12. To do so, a surgeon may first resect the proximal end 170 of the patient's humeral bone 172 to remove the patient's natural humeral head (not shown) and create a planar resected surface 174. The surgeon may select a desired version angle for the resected surface 174 according to any known technique. The surgeon may then select a canal reamer (not shown) t to define a passageway 176 in the humeral canal. It should be appreciated that more than one canal reamer may be used to progressively define the passageway 176 in the bone 172.

The surgeon may then select a brosteotome 10 that has an elongated stem 20 that matches the diameter of the final canal reamer use to create the passageway 176. As shown in FIG. 8, the surgeon may place the stem 20 of the brosteotome 10 in the passageway 176 and orient the version. One method of orienting the version includes passing a pin 136 through any of the alignment holes 36, 44 defined in the brosteotome 10. If the hole 44 is used, the brosteotome 10 may be oriented such that the pin it lies flat on the resected surface 174. If any of the holes 36 are used, the pin may be aligned with the axis of the forearm of the patient.

When the brosteotome 10 is positioned at the desired version, the pin 136 may be removed from the alignment hole and placed in the depth stop hole 134 defined in the brosteotome body 14. The surgeon may then tap on the strike plate 14 with a mallet to advance the brosteotome 10 into the proximal end 170 of the bone 172. As the brosteotome 10 advances downward, the anterior cutting teeth 54 and the posterior cutting teeth 58 are advanced into contact with the bone 172. The anterior cutting teeth 54 and the posterior cutting teeth 58 define tapered channels 180 that extend outwardly from the passageway 176, as shown in FIG. 10. Each channel 180 is sized to receive one of the fins 150, 152 of the humeral prosthetic component 12.

The medial cutting teeth 50 of the brosteotome 10 are also advanced into contact with the patient's bone 172 to remove bone from the medial side 182 of the passageway 176. As described above, the longitudinal axis 48 of the brosteotome elongated body 14 defines the axis of insertion of the brosteotome 10 during the procedure. Because the outer surfaces 76 of the cutting teeth 50 extend parallel to the axis 48, resected bone is advanced upward along the outer surfaces 76 parallel to the axis of insertion, thereby facilitating the resecting process. The resected bone is then advanced into the distal-facing openings 108 of the slots 106 and upward along the slots 106. The arced configuration of the teeth 50 define an arced medial surface 190 of the patient's bone 172. The brosteotome 10 may be driven into the bone 172 until the pin 136 touches the resected surface 174, as shown in FIG. 9.

The brosteotome 10 may then be removed from the bone. As shown in FIG. 10, the process of impacting or driving the brosteotome 10 into the bone 172 forces particles and pieces of resected bone 192 into the slots 106 defined between the cutting teeth 50. As the brosteotome 10 was driven into the bone, the resected bone 192 was compacted into a wafer 200 positioned in each slot 106. Each wafer 200 has sufficient cohesion to permit the wafer to be removed from the slot 106 and utilized in a bone graft impaction process.

Figure 11:
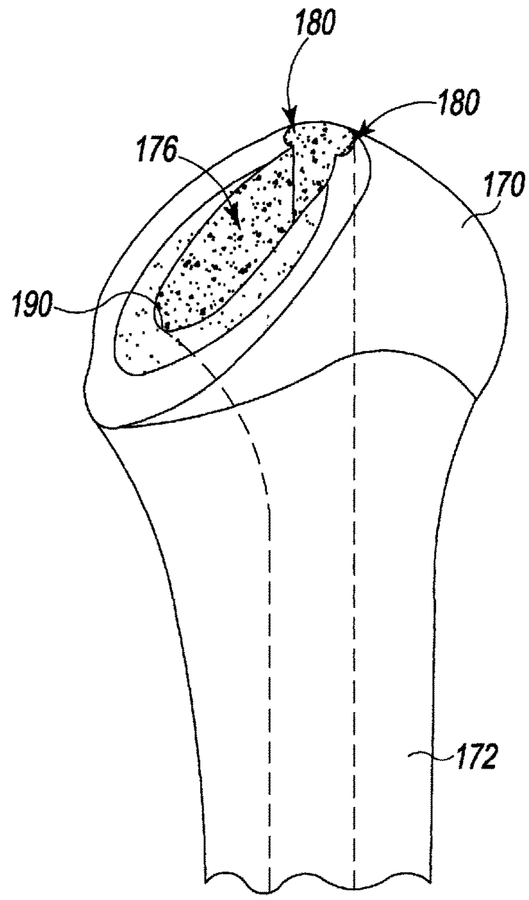
FIG. 11 is a perspective view of the patient's humeral bone after it has been prepared to receive the humeral prosthetic component of FIG. 5.

After the brosteotome 10 is removed from the bone 172, the passageway 176 has been shaped to receive the humeral prosthetic component 12. As shown in FIG. 11, the bone 172 includes the arced medial surface 190, which substantially matches the curved medial surface 122 of the prosthetic component 12. Additionally, as described above, a pair of tapered channels 180 extend outwardly from the passageway 176, and each channel 180 is sized to receive one of the fins 150, 152 of the humeral prosthetic component 12. The surgeon may then proceed with subsequent surgical steps, including, for example, trialing and implantation of the prosthetic components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument for preparing a patient's humeral bone to receive an orthopaedic implant, the instrument comprising:

an elongated body having a longitudinal axis extending through a distal end and a proximal end, a first plurality of cutting teeth extending outwardly from an anterior surface of the elongated body, a second plurality of cutting teeth extending outwardly from a posterior surface of the elongated body, a plurality of medial cutting teeth extending from a medial side of the elongated body, each medial cutting tooth comprising (i) a first curved medial edge, and (ii) a curved outer surface that extends distally from the first curved medial edge to a second curved medial edge, wherein the curved outer surface of each medial cutting tooth extends parallel to the longitudinal axis of the elongated body when the instrument is viewed in a coronal plane, and a slot defined between each pair of adjacent medial cutting teeth of the plurality of medial cutting teeth, each slot including a distal-facing opening, wherein each slot is defined between a planar distal surface and a planar proximal surface that extends parallel to the planar distal surface.

2. The orthopaedic surgical instrument of claim 1, wherein:

an imaginary line extends through a medial-most point of the first curved medial edge and a medial-most point of the second curved medial edge of each medial cutting tooth, and the imaginary line of each medial cutting tooth extends parallel to the longitudinal axis of the elongated body and is spaced apart from the imaginary lines defined by the other medial cutting teeth.

3. The orthopaedic surgical instrument of claim 2, wherein:

the plurality of medial cutting teeth includes a distal-most medial cutting tooth, and the imaginary line of the distal-most medial cutting tooth is positioned laterally of the imaginary line of any other medial cutting tooth of the plurality of medial cutting teeth.

4. The orthopaedic surgical instrument of claim 1, wherein the planar distal surface and the planar proximal surface of each slot extend parallel to the planar distal surfaces and the planar proximal surfaces of the other slots.

5. The orthopaedic surgical instrument of claim 1, wherein an angle is defined between each planar distal surface and the longitudinal axis of the elongated body when the instrument is viewed in the coronal plane, the angle having a magnitude of 45 degrees.

6. The orthopaedic surgical instrument of claim 1, wherein a curved base surface connects the planar distal surface to the planar proximal surface.

7. The orthopaedic surgical instrument of claim 1, wherein:

each slot has a height defined by an imaginary line extending orthogonal to the planar distal surface and the planar proximal surface, and each medial cutting tooth has a thickness defined between a medial-most point of its first curved medial edge and a medial-most point of its second curved medial edge, the thickness of each medial cutting tooth being less than the height of each slot.

8. The orthopaedic surgical instrument of claim 7, wherein the thicknesses of the medial cutting teeth are equal.

9. The orthopaedic surgical instrument of claim 1, wherein the curved outer surface of each medial cutting tooth extends from the anterior surface to the posterior surface of the elongated body.

10. The orthopaedic surgical instrument of claim 1, further comprising a handle extending from the proximal end of the elongated body and a proximal strike plate attached to the handle.

11. The orthopaedic surgical instrument of claim 10, further comprising a distal stem removeably coupled to the distal end of the elongated body.

12. An orthopaedic surgical instrument for preparing a patient's humeral bone to receive an orthopaedic implant, the instrument comprising:

an elongated body having a longitudinal axis extending through a distal end and a proximal end, a plurality of cutting teeth are extending from a medial side of the elongated body, each cutting tooth comprising (i) a first curved medial edge, and (ii) a curved outer surface that extends distally from the first curved medial edge to a second curved medial edge, and a distal stem coupled to the distal end of the elongated body, wherein when the instrument is viewed in a coronal plane, (i) the curved outer surface of each medial cutting tooth extends parallel to the longitudinal axis of the elongated body, and (ii) an arced imaginary line is defined by the medial-most points of the second curved medial edges of the cutting teeth, and wherein the elongated body has a lateral surface positioned opposite the medial surface that is devoid of cutting teeth.

13. The orthopaedic surgical instrument of claim 12, further comprising a handle extending from the proximal end of the elongated body and a proximal strike plate attached to the handle.

14. The orthopaedic surgical instrument of claim 12, further comprising:

a first plurality of tapered cutting teeth extending outwardly from an anterior surface of the elongated body, and a second plurality of tapered cutting teeth extending outwardly from a posterior surface of the elongated body.

15. A method of preparing a patient's humeral bone to receive an orthopaedic implant, the method comprising:

coupling a distal stem to a distal end of an elongated body of an orthopaedic surgical instrument, inserting the orthopaedic surgical instrument into the patient's humeral bone to define a cavity sized to receive the orthopaedic implant, the orthopaedic surgical instrument including (i) a plurality of medial cutting teeth positioned to define a curved medial surface in the patient's humeral bone, (ii) a plurality of anterior cutting teeth to define a first tapered groove of the cavity, and (iii) a plurality of posterior cutting teeth to define a second tapered groove on a posterior side, and inserting the orthopaedic implant into the cavity such that a first keel of the orthopaedic implant is received in the first tapered groove and a second keel of the orthopaedic implant is received in the second tapered groove, the orthopaedic implant further including a curved medial surface that substantially matches the curved medial surface defined by the plurality of medial cutting teeth of the orthopaedic surgical instrument.

16. The method of claim 15, wherein inserting the orthopaedic surgical instrument includes inserting the elongated body and the distal stem into the patient's humeral bone.

17. The method of claim 15, further comprising removing a bone wafer from a slot defined between a pair of medial cutting teeth.

* * * * *